United States Patent [19]

Cherian

[11] Patent Number: 5,216,700
[45] Date of Patent: Jun. 1, 1993

[54] TAPE HAVING GRADUATED SCALE PROVIDING LOCATION INDICIA DURING X-RAY PROCESSES

[76] Inventor: George Cherian, 5136 W. 60th Terrace, Mission, Kans. 66205

[21] Appl. No.: 836,252
[22] Filed: Feb. 18, 1992
[51] Int. Cl.⁵ .............................................. H05G 1/28
[52] U.S. Cl. .................................. 378/163; 378/164; 378/205; 128/653.4; 128/654
[58] Field of Search ............... 378/162, 163, 164, 205, 378/206; 128/653.4, 654

[56] References Cited

U.S. PATENT DOCUMENTS

| | | | |
|---|---|---|---|
| 2,650,308 | 8/1953 | Catlin | 378/163 |
| 3,812,842 | 5/1974 | Rodriguez | 378/163 |
| 4,506,676 | 3/1985 | Duska | 378/162 |
| 4,860,331 | 8/1989 | Williams et al. | 378/163 |
| 4,915,112 | 4/1990 | Singer | 378/163 |

Primary Examiner—David P. Porta
Assistant Examiner—Kim-Kwok Chu
Attorney, Agent, or Firm—Kokjer, Kircher, Bowman & Johnson

[57] ABSTRACT

Tape which is used to mark the location of arterial blockage or other medical problems on x-ray film. The tape has a T-shaped configuration and includes a flat main body and a rib projecting from the main body. The main body of the tape strip has an adhesive layer on one side which is initially covered by a cover strip. When the cover strip is removed, the strip can be adhesively attached to a patient who is to be x-rayed. The rib has graduation marks that are opaque to x-rays and are thus reproduced on the x-ray film to correlate the location of the medical problem with the marks during subsequent treatment. The rib can be folded flatly against the main body of the tape strip and held adhesively in that position so that the graduation marks are useful when x-rays are taken in two different dimensions.

8 Claims, 1 Drawing Sheet

TAPE HAVING GRADUATED SCALE PROVIDING LOCATION INDICIA DURING X-RAY PROCESSES

FIELD OF THE INVENTION

This invention relates generally to medical x-ray processes and more particularly to a tape which is provided with graduation marks that are opaque to x-rays so that the tape can be used in the x-ray process to indicate the location of images on the x-ray film.

BACKGROUND OF THE INVENTION

In many types of x-ray processes, it is necessary to provide on the x-ray film an indication of the location of the images that appear on the film. For example, it is common practice to inject dye into the bloodstream to locate arterial blockage. The dye is visible on the x-ray film and indicates the location of the blockage. Surgical or other techniques are then used to alleviate the blockage. In order to assure that incisions and other surgical procedures are carried out at the correct location, it is necessary for the location of the blockage on the x-ray film to be correlated with the body part in which the blockage occurs.

In the past, the common practice has been to place a ruler or other measuring stick with graduation marks that are opaque to x-rays against the body and then take the x-rays. The graduation marks are visible on the exposed x-ray film and indicate the location of the blockage or other problem.

One problem with this technique is that it is often inaccurate because the ruler or other measuring stick can move on the patient between the time of the x-rays and the time of the treatment. The ruler must also be sterilized prior to each use, and this takes the valuable time of hospital technicians or other personnel. The sterilization may be done improperly or incompletely, and this can create significant problems. At best, the use of a ruler is a problematical solution and at worst it is inaccurate and possibly even dangerous. The devices that have been used in the past are useful in only one place. Because accurate location usually requires views in two different planes, two different devices must be used if radiographs in two planes are required.

SUMMARY OF THE INVENTION

The present invention has, as its principal goal, the provision of a reliable and accurate means for indicating the location of x-ray images relative to the body part which is subjected to the x-ray process.

In accordance with the invention, tape having a T-shaped configuration includes a flat tape body with a layer of adhesive on one side and a rib projecting from the center of the other side. The adhesive layer is covered by a removable cover strip which can be removed to allow the tape to be adhesively attached to the body part that is to be x-rayed. The rib is provided with a graduated scale including graduation marks that are opaque to x-rays. The rib normally extends perpendicular to the main body of the tape strip. When x-rays are directed parallel to the tape strip, the graduation marks provide images on the x-ray film that correlate the location of the blockage or other x-ray image with the body part to which the tape is applied.

The rib can be flexed from its normal position until it lies along the tape strip. Adhesive areas on the rib are initially covered by cover patches which can be removed to permit the rib to be folded against the strip and held against it by the adhesive. Then, the graduation marks provide images on the x-ray film when the x-rays are directed perpendicular to the tape strip. In this manner, a single piece of tape can be used to provide a indication in two different dimensions of the location of the problem area relative to the tape on the exterior of the body part. Commonly, x-rays are projected in different directions, and this is greatly facilitated by the tape of the present invention. Consequently, use of the tape allows surgery and other types of treatment to be performed accurately and efficiently.

DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figure 1:
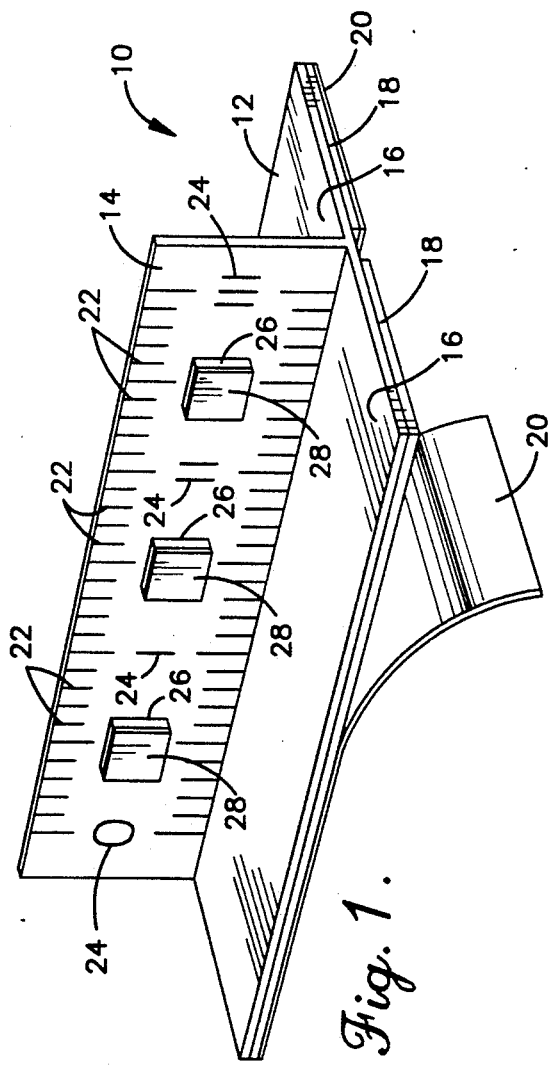
FIG. 1 is a perspective view of a strip of tape constructed according to a preferred embodiment of the present invention, with one of the cover strips partially peeled away from the adhesive which is carried on one side of the tape strip.

Referring now to the drawings in more detail and initially to FIG. 1, numeral 10 generally designates a tape strip which is constructed in accordance with the present invention. The tape 10 has a T-shaped configuration and includes a flat main tape body 12 and a flat rib 14 which projects from one side of the tape body 12 and is normally perpendicular to it. The body 12 of the tape strip includes two flat flanges 16 which are located on opposite sides of the rib 14. The tape 10 may be constructed of any suitable material of the type commonly used for flexible tapes. The material of which the tape strip is constructed should be transparent to x-rays.

The surface of each flange 16 opposite the surface from which the rib 14 projects is provided with a layer of adhesive 18. The adhesive 18 may be of any suitable type that adheres to the tape body 12 and also to the human skin when applied to it. Each of the adhesive layers 18 is initially covered by a cover strip 20 which may be coated paper or any other suitable material. The adhesive layers 18 are thus sandwiched between flanges 16 and the cover strips 20. Each cover strip 20 is removable and can be peeled away from the adhesive layer 18 when the tape is to be used.

One and preferably both sides of the rib 14 bear a graduated scale which includes a plurality of spaced apart graduation marks 22. As shown in FIG. 1, the marks 22 are preferably located along each longitudinal edge of the rib 14, and some of the marks are longer than others, with the longer marks dividing the graduated scale into increments of five graduation marks 22. The scale may be in inches, centimeters or any other units.

Printed indicia 24 are provided o the graduated scale or scales. The initial one of the indicia 24 is aligned with the "zero" graduation marks and may take the form of the numeral 0. The next indicator is aligned with the tenth graduation marks 22 and may take the form of the Roman numeral I. The third indicator is aligned with the twentieth graduation marks 22 and may take the form of Roman numeral II. The fourth and final indicator 24 may take the form of Roman numeral III, and it is aligned with the thirtieth graduation marks. The graduation marks 22 and all of the indicia 24 are opaque to x-rays. The scale may include any number of marks 22 and any number of indicia 24 and the tape may be of any length and the marks identified accordingly.

If a graduated scale is provided on both sides of the rib 14, the graduation marks 22 on the opposite sides are aligned with one another. In addition, the indicia 24 on opposite sides of the rib are aligned with identical indicia on the opposite side of the rib. Instead of the marks described above, numerals or any other system of graduation may be used.

One and preferably both sides of the rib 14 are provided with a plurality of relatively small adhesive patches 26. The areas at which the adhesive 26 is applied to the rib 14 are spaced apart along the length of the rib. Each of the adhesive patches 26 is initially covered by a cover patch 28 which may be coated paper or some other suitable material that can be removed from the adhesive 26.

The tape strip 10 may initially form part of a roll of tape, or the tape may be packaged in any other convenient form. If packaged in a roll, the rib 14 lies flatly against one of the flanges 16 in the roll. When the tape is unwound from the roll, the rib 14 flexes toward its normal position which is the position shown in FIGS. 1 and 3 in which the rib is perpendicular to the tape body 12. The tape can be unwound from the roll and cut to the desired length.

Figure 2:
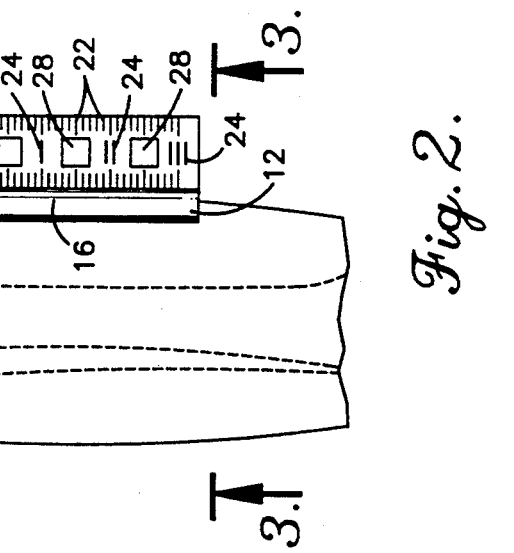
FIG. 2 is a front elevational view showing the strip of tape applied to the leg of a patient.

In use, the tape 10 provides an indication of the location of arterial blockage or other medical problem areas. For example, when x-rays are to be taken of a human leg 30, the tape is applied to the leg before the x-rays are taken. The tape is applied by removing the cover strips 20 from the adhesive layers 18 and then pressing the adhesive side of the tape strip against the portion of the leg which is to be x-rayed. As shown in FIG. 2, the tape may be applied to the side of the leg, and the adhesive layers 18 adhesively secure the main body 12 against the leg in the area that is to be subjected to x-rays.

Figure 3:
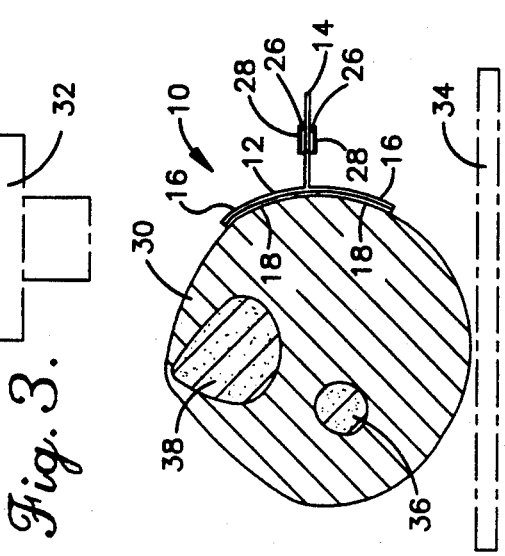
FIG. 3 is a sectional view taken generally along line 3—3 of FIG. 2 in the direction of the arrows and depicting an x-ray process in which x-rays are directed generally parallel to the main body of the tape strip.

With particular reference to FIG. 3, an x-ray machine 32 located to the front of the leg 30 is oriented to direct x-rays toward film 34 positioned behind the leg. The x-rays are thus directed generally parallel to the plane of the main body 12 of the tape strip and perpendicular to the rib 14. When the x-ray film is developed, the graduation marks 22 are reproduced as images on the film and can be correlated on the film with the location of the problem area which may be a blockage in an artery 36 or damage to a bone 38. When the x-rays are directed parallel to the main body 12, the rib 14 is in its normal position extending generally perpendicular to the main body 12.

Figure 4:
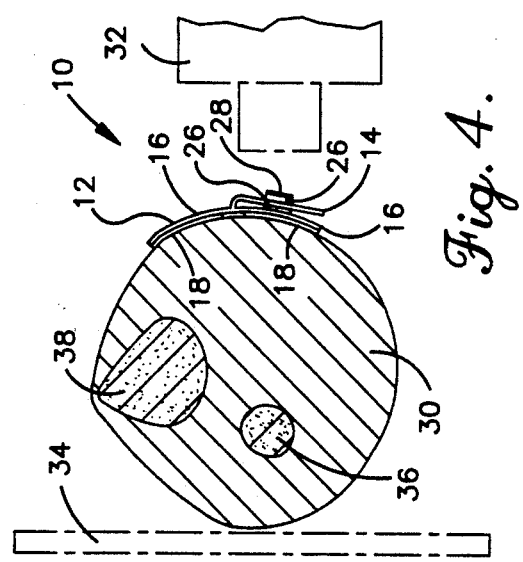
FIG. 4 is a sectional view similar to FIG. 3, but depicting an x-ray process in which the x-rays are directed generally perpendicular to the main body of the tape strip, with the rib folded and secured against the strip.

With reference now to FIG. 4, the x-ray machine 32 can subsequently be moved to the side of the leg and the film 34 can be moved to the opposite side. The cover patches 28 may be removed from the adhesive patches 26, and the rib 14 can be flexed from its normal position until it lies generally along one of the flanges 16 with the adhesive patches 26 pressed against the flange 16 in order to hold the rib 14 in this position. The x-rays are directed generally perpendicular to the main body 12 of the tape strip and thus perpendicular to the rib 14. Again, the graduation marks 22 provide images on the film 34 which indicate the location of any problem areas that show up as images on the x-ray film.

In this manner, the tape strip 10 can be used to indicate the location in two different dimensions of any arterial blockage or other problem internally of the leg 30. Because of the flexibility of the rib 14, it can be positioned in two different positions in order to accommodate the different directions at which the x-rays are oriented during the x-ray process.

The indicia 24 are opaque to x-rays, and the entire graduated scale, including all of the graduation marks 22 and all of the indicia 24, thus provide images on the exposed x-ray film. The indicia 24 are used to identify the graduation marks 22 so that mistakes are not made depending upon whether the tape is applied with either end up. Because the graduation marks 22 on the opposite sides of the rib 14 are aligned with one another, and because the indicia 24 appear the same regardless of which side the rib is viewed from, the tape can be used with the rib 14 folded down against either of the flanges 16 without creating inaccuracies or other problems.

The tape 10 remains in place during the surgical procedure or other technique that is used to alleviate the problem. For example, if the x-ray film indicates that there is a blockage in the area of the tenth graduation mark 22 (the mark adjacent to the I indicia), the surgeon can make an incision in alignment with this particular graduation mark because it is known that this will be the proper area to provide access to the problem area. The problem area can similarly be located when other medical techniques are used to alleviate the problem.

Although use of the tape 10 has been described in connection with application to a leg 30, it is to be understood that the tape ca be applied to other body parts that are to be subjected to x-rays and subsequent treatment.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. Tape for use during exposure of x-ray film in a medical x-ray process, comprising:
   a flexible tape strip having adhesive on one side for adhesive attachment of the tape strip to a body part;
   a rib projecting from said strip on a side thereof opposite said one side, said rib having a first position oriented generally perpendicular to said strip and being flexible from said first position to a second position lying generally along the strip;

means for retaining said rib in the second position when flexed thereto; and a graduated scale on said rib including a plurality of graduation marks spaced along the length thereof, said marks being opaque to x-rays to provide an image on the x-ray film when x-rays are directed generally parallel to the strip in the first position of the rib and generally perpendicular to the strip in the second position of the rib.

2. The tape of claim 1, wherein said retaining means includes a plurality of adhesive areas spaced along said rib for adherence to said tape strip when applied thereto.

3. The tape of claim 2, including a plurality of removable cover patches on the respective adhesive areas.

4. The tape of claim 1, including a removable cover strip on said adhesive.

5. The tape of claim 1, including a plurality of indicia on said graduated scale for identifying the graduation marks, each of said indicia comprising a mark on said rib opaque to x-rays and having the same appearance when viewed from either side of said rib.

6. Tape for use during an x-ray process carried out on a body part to expose x-ray film, comprising:

a T-shaped tape strip having a flexible tape body and a rib extending from the tape body, said tape body having an adhesive side for adhesive attachment to a preselected location on said body part;

said rib having a normal first position wherein the rib extends generally perpendicular to the tape body and being flexible from the first position to a second position wherein the rib lies generally along the tape body;

adhesive means on said rib for retaining the rib in its second position when flexed thereto; and a graduated scale including a plurality of spaced apart graduation marks on said rib which are opaque to x-rays, whereby the marks provide an image on x-ray film exposed to x-rays directed generally parallel to the tape body with said rib in the first position and also on x-ray film exposed to x-rays directed generally perpendicular to the tape body with said rib in the second position, thereby indicating the location of other images on the film relative to each graduation mark in two dimensions.

7. The tape of claim 6, including a plurality of indicia on said graduated sc le for identifying the graduation marks, each of said indicia comprising a mark on said rib opaque to x-rays and having the same appearance when viewed from either side of said rib.

8. The tape of claim 6, wherein said adhesive means comprises a plurality of adhesive areas on said rib for adherence to said tape body when applied thereto, each adhesive area being covered by a removable cover patch.

* * * * *